US006803057B2

(12) United States Patent
Ramirez et al.

(10) Patent No.: US 6,803,057 B2
(45) Date of Patent: *Oct. 12, 2004

(54) HYDROGEN PEROXIDE DISINFECTANT WITH INCREASED ACTIVITY

(75) Inventors: Jose A. Ramirez, Mississauga (CA); Michael J. Rochon, Caledon (CA)

(73) Assignee: Virox Technologies Inc., Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/028,373

(22) Filed: Dec. 28, 2001

(65) Prior Publication Data

US 2002/0192297 A1 Dec. 19, 2002

Related U.S. Application Data

(63) Continuation-in-part of application No. 09/356,345, filed on Jul. 19, 1999, now Pat. No. 6,346,279.
(60) Provisional application No. 60/112,047, filed on Dec. 14, 1998.

(51) Int. Cl.$^7$ .................. A01N 59/00; A01N 59/26; A01N 41/04; A01N 25/22; A61L 2/18
(52) U.S. Cl. .................. 424/616; 424/601; 424/602; 424/603; 424/604; 424/605; 424/606; 424/126; 424/DIG. 6; 514/75; 514/102; 514/108; 514/112; 514/114; 514/140; 514/141; 514/142; 514/143; 514/529; 514/547; 514/549; 514/550; 514/552; 514/553; 514/557; 514/558; 514/559; 514/560; 514/574; 514/576; 514/578; 514/709; 514/711; 514/970; 514/973; 422/12; 422/28; 504/151
(58) Field of Search .................. 424/601–606, 424/616, 126, DIG. 6; 422/12, 18; 514/553, 557, 558, 559, 560, 574, 576, 709, 970, 75, 102, 108, 112, 114, 140, 141, 142, 143, 529, 547, 549, 550, 552, 578, 711, 973; 504/151

(56) References Cited

U.S. PATENT DOCUMENTS

| | | | |
|---|---|---|---|
| 4,051,058 A | 9/1977 | Bowing | 424/616 |
| 4,405,482 A | 9/1983 | Hayes et al. | 510/307 |
| 4,477,438 A | 10/1984 | Willcockson et al. | 424/616 |
| 4,518,585 A | 5/1985 | Greene et al. | 424/616 |
| 5,059,417 A | 10/1991 | Williams et al. | 424/616 |
| 5,171,564 A | 12/1992 | Nathoo et al. | 424/613 |
| 5,200,189 A | 4/1993 | Oakes et al. | 424/405 |
| 5,264,229 A | 11/1993 | Mannig et al. | 426/335 |
| 5,523,012 A | 6/1996 | Winterton et al. | 424/78.04 |
| 5,641,530 A | 6/1997 | Chen | 426/532 |
| 5,723,406 A | 3/1998 | Larose et al. | 504/114 |
| 5,736,498 A | 4/1998 | Gray | 510/372 |
| 5,900,256 A | 5/1999 | Scoville, Jr. et al. | 514/557 |
| 6,043,209 A | 3/2000 | Micciche et al. | 510/280 |
| 6,346,279 B1 * | 2/2002 | Rochon | 424/616 |
| 2002/0142051 A1 * | 10/2002 | Rochon | 424/616 |
| 2003/0078178 A1 * | 4/2003 | Ramirez et al. | 510/309 |
| 2003/0180377 A1 * | 9/2003 | Ramirez et al. | 424/616 |

FOREIGN PATENT DOCUMENTS

| | | |
|---|---|---|
| EP | 0057153 | 4/1986 |
| EP | 0087049 | 11/1986 |
| EP | 0289463 | 11/1988 |
| EP | 351772 | 1/1990 |
| EP | 0845526 | 6/1998 |
| GB | 2101350 | 1/1983 |
| JP | 57192302 | 8/1982 |
| JP | 9087677 | 3/1997 |
| JP | 10121097 | 5/1998 |
| JP | 10130693 | 5/1998 |
| WO | WO9314183 | 9/1993 |
| WO | WO9811777 | 3/1998 |
| WO | WO98/18894 | 5/1998 |
| WO | WO9821305 | 4/1999 |

OTHER PUBLICATIONS

Baldry, M..G.C., "The bactericidal, fungicidal and sporicidal properties of hydrogen perioxide and peracetic acid", Journal of Applied Bacteriology, 34, 417–423, and especially p. 418 (top left column) and 421 (top right column) thereof, 1983.

Sattar S.A., Springthrope, S. and M. Rochon, "A product based on accelerated and stabilized hydrogen peroxide, evidence for broad–spectrum germicidal activity", Can. J. Infection Control, Winter 1998.

Lopes, J.A., "Evaluation of dairy and food plant sanitizers against *Salmonella typhimurium* and *listeria* momocytogenes", J. Dairy Sci., 69, 2791–2796, 1986.

Disinfection, Sterilization and Preservation, 4$^{th}$ ed. Seymour S. Block, Lea & Febinger 1991, pp. 167–172, 178–180, 256–261, 263–271.

* cited by examiner

Primary Examiner—John Pak
(74) Attorney, Agent, or Firm—Clark & Brody

(57) ABSTRACT

An acidic aqueous hydrogen peroxide solution is provided with improved disinfectant activity. Concentrated solutions preferably contain up to about 8 wt./wt. % H2O2 and as-used concentrations contain about 0.5% wt./wt. % H2O2. The solution also contains from 0.05 to 8.0 wt./wt. % of at least one phosphorous-based acid, e.g. phosphoric acid and/or a phosphonic acid with from 1 to 5 phosphonic acid groups, and from 0.02 to 5 wt./wt. % of at least one anionic surfactant. The surfactant is selected from C8 to C16 alkyl aryl sulfonic acids, sulfonated C12 to C22 carboxylic acids, C8 to C22 alkyl diphenyl oxide sulfonic acids, naphthalene sulfonic acids, C8 to C22 alkyl sulfonic acids, and alkali metal and ammonium salts thereof, and alkali metal C8 to C18 alkyl sulfates, and mixtures thereof. Most preferably the solution has an emulsifier and/or hydrotrope, e.g. an alkylated sulfonated diphenyl oxide salt, an alkyl aryl polyoxyethylene surfactant, and/or a polyoxyethylene surfactant. The solution may also contain corrosion inhibitors and/or lower alcohols.

21 Claims, No Drawings

HYDROGEN PEROXIDE DISINFECTANT WITH INCREASED ACTIVITY

This application is a continuation-in-part of U.S. patent application Ser. No. 09/356,345 filed Jul. 19, 1999 now U.S. Pat. No. 6,346,279, which claims the benefit of U.S. provisional patent application 60/112,047 filed Dec. 14, 1998.

FIELD OF THE INVENTION

The present invention relates to disinfectants and, in particular, it relates to hydrogen peroxide solutions with improved disinfectant and antimicrobial properties.

BACKGROUND TO THE INVENTION

A wide range of disinfectants is known, as discussed for example in Disinfection, Sterilization, and Preservation, edited and partially written by Professor Seymour S. Block, Fourth Edition, published 1991 by Lea & Febiger, Pennsylvania. Certain peroxygen compounds, chlorine compounds, phenolics, quaternary ammonium compounds and surface active agents are known for their germicidal properties. The rate of disinfection is relatively slow in many cases, and some compounds emit volatile organic compounds or leave a persistent residue in the environment.

Hydrogen peroxide is finding favour in many applications because its breakdown products, water and oxygen, are innocuous, and it tends to have broad spectrum antimicrobial activity. Broad spectrum activity is important in situations where harmful organisms are present but their identity is not known.

As hydrogen peroxide tends to be unstable and decomposes over time, steps must be taken to stabilize the hydrogen peroxide solutions for storage purposes. Various ways have been proposed to improve the stability of hydrogen peroxide compositions. For example, sodium stannate, sodium nitrate, and diethylene triamine penta (methylenephosphonic acid) have been reported as being useful as stabilizers, as disclosed in U.S. Pat. No. 5,523,012 to Winterton et al., which issued Jun. 4, 1996.

A major drawback of most disinfectants used heretofore has been the length of time needed to reduce the bacterial count after the disinfectant has been applied to a bacterially contaminated material. For example, it may take 30 minutes or more after application of the disinfectant to disinfect a treated surface. In many circumstances this rate of disinfection is far from satisfactory.

Combinations of hydrogen peroxide with various surfactants are known. For example, Winterton et al. discloses, in U.S. Pat. No. 5,523,012, a buffered disinfecting solution for contact lenses, which has from about 0.1% to about 1.0% of an ocularly compatible surfactant. Winterton discloses that, in one experiment, addition of about 0.4% anionic sulfosuccinate surfactant improved the killing time for *aspergillus fumigatus* to 6.9 minutes, compared to 9.4 minutes for a solution containing 0.1% nonionic surfactants. However, even 6.9 minutes is far too long for many applications.

The present invention is directed to improving the efficacy of hydrogen peroxide based solutions.

SUMMARY OF THE INVENTION

Accordingly, the invention provides an aqueous solution having a pH of from about 0.5 to about 6 and comprising i) hydrogen peroxide in a concentration of from about 0.01 to about 20 wt./wt. % of the solution, ii) at least one phosphorus-based acid in a concentration range of from about 0.05 to about 8 wt./wt. % of the solution, and iii) at least one anionic surfactant selected from the group consisting of C8 to C16 alkyl aryl sulfonic acids and alkali metal, ammonium, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkali metal, ammonium, calcium and magnesium C8 to C18 alkyl sulfates, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 5 wt./wt. % of the solution.

The phosphorus-based acid may be selected from the group consisting of the derivatives of phosphorous oxides in which the phosphorous atom is in the +5 oxidation state, phosphonic acids having 1 to 5 phosphonic acid groups and salts thereof, and mixture thereof. Preferably, the phosphorus-based acid is selected from the group consisting of phosphoric acid, 1-hydroxyethylidene-1,1,-diphosphonic acid, and mixtures thereof.

The solution may contain an additional component selected from the group consisting of emulsifiers, hydrotropes, detergents and mixtures thereof in a concentration of up to about 3 wt./wt. % of the solution, and preferably in a concentration of from about 0.04 to about 3 wt./wt. % of the solution. The emulsifiers and detergents may be polyoxyethylene surfactants. The hydrotrope may be selected from the group consisting of alkylated sulfonated diphenyl oxides, alkylated sulfonated diphenyl oxide salts, and mixtures thereof, and preferably is a C6 alkylated sulfonated diphenyl oxide disodium salt.

The anionic surfactant is preferably dodecyl benzene sulfonic acid or an alkali metal salt or ammonium salt thereof.

Preferably, the hydrogen peroxide concentration may be from about 0.05 to about 8 and, more preferably from about 0.5 to about 8, wt./wt. % of the solution.

Also preferably, the phosphorus-based acid may be present in a concentration of from about 0.2 to about 8 wt./wt. % of the solution.

The anionic surfactant is preferably present in a concentration of from about 0.08 to about 5 wt./wt. % of the solution.

Preferably, the pH of the solution is from about 0.7 to about 3.5.

The solution may further contain a corrosion inhibitor in a concentration of from about 0.05 to about 10 wt./wt % of the solution. Also, the solution may contain a monocarboxylic acid, a polycarboxylic acid, or mixtures thereof, in a concentration of from about 0.05 to about 4 wt./wt. % of the solution. The solution may also contain an alcohol comprising one to six carbon atoms in a concentration of from about 0.1 to about 10 wt./wt. % of the solution.

In accordance with another aspect of the invention, the present solution may be made in concentrated form for dilution by the end user with water.

In accordance with a further aspect, the invention provides a powdered formulation which can be diluted with water to produce the present aqueous solution.

DETAILED DESCRIPTION OF PREFERRED EMBODIMENTS

In the past few years, efforts have been concentrated on developing chemicals that will be highly effective against microorganisms when highly diluted, will be low in toxicity to humans and other animals, and will not injure the environment. Of all the known disinfectants and antimicrobials, hydrogen peroxide appears to have exceptional potential, especially in terms of toxicity and injury to the environment because the decomposition products are benign. For example, at concentrations of 1–3 wt./wt. % aqueous solution, hydrogen peroxide is considered non-corrosive and non-irritating; at concentrations of 3–7 wt./wt. % aqueous solution, hydrogen peroxide is considered non-corrosive but an eye irritant; and at concentrations of above about 8 wt./wt. % aqueous solution, hydrogen peroxide is considered corrosive, more so at higher concentrations, and also a strong oxidizing agent.

The higher concentration levels of hydrogen peroxide solutions required to provide fast, effective action are not practical or economically viable, may be subject to hazardous goods regulations and require special precautions for handling and use. Heretofore, one of the major drawbacks of hydrogen peroxide, in low concentrations, is that its antimicrobial action is too slow. A second major drawback is that it has not been considered possible to stabilize the peroxide sufficiently to make the solution commercially acceptable. For example, prior references indicate that a 0.1 wt./wt. % aqueous solution of hydrogen peroxide requires 60 minutes to disinfect surfaces contaminated with *staphylococcus aureus*, whereas a 25.8 wt./wt. % aqueous solution of hydrogen peroxide requires only 20 seconds to disinfect surfaces contaminated with *staphylococcus aureus*. The latter solution is clearly unacceptable for commercial use, both from a safety standpoint and an economic standpoint.

It has now been found that the addition of phosphorus-based acids and certain anionic surfactants greatly, and surprisingly, enhances the bactericidal and/or virucidal activity of aqueous hydrogen peroxide solutions. The phosphorus-based acids are inorganic acids or organic acids. Especially preferred are phosphorus-based acids selected from the group consisting of the derivatives of phosphorous oxides in which the phosphorous atom is in the +5 oxidation state and phosphonic acids having 1 to 5 phosphonic acid groups and salts thereof.

More preferably, the phosphorous based acids are phosphoric acid ($H_3PO_4$), sodium tripolyphosphate, and phosphonic acids consisting of 1-hydroxyethylidene-1,1,-diphosphonic acid, amino tri(methylene phosphonic acid), diethylenetriaminepenta-(methylene phosphonic acid), 2-hydroxyethylimino bis(methylene phosphonic acid), ethylene diamine tetra(methylene phosphonic acid). Each may be used alone but mixtures of phosphoric acid and at least one of the phosphonic acids are preferred. Some of these phosphonic acids are available from Albright & Wilson under the trade mark BRIQUEST and some from Solutia Inc. under the trade mark DEQUEST.

The preferred phosphorous based acids are also known for their sequestering properties and serve, advantageously, to stabilize the solution against hydrogen peroxide degradation. These stabilizing properties are particularly important in respect of solutions containing higher concentrations of hydrogen peroxide which tend to break down quickly. Thus, solutions of the present invention also have a long shelf life, e.g. up to a year or more.

Solutions according to the invention have phosphorus-based acids in a concentration of from about 0.05 to about 8.0 wt./wt. % of the solution, preferably from about 0.20 to about 8 wt./wt. %, and more preferably from about 0.20 to about 6 wt./wt. %. The solution may be ready-to-use or concentrated so as to require dilution by the end user. The lower concentrations are used in ready-to-use formulations, while higher concentrations are used in commercial liquid concentrates.

The anionic surfactant enhances the bactericidal activity of the solution and is selected from the group consisting of C8 to C16 alkyl aryl sulfonic acids and alkali metal, ammonium, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkali metal, ammonium, calcium and magnesium C8 to C18 alkyl sulfates, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof.

Of the listed anionic surfactants, the C8 to C16 alkyl aryl sulfonic acids and their aforesaid salts are preferred as they are widely available and relatively inexpensive. They are also biodegradable. Preferred alkyl aryl sulfonic acids and their salts are dodecyl benzene sulfonic acid, and tridecyl benzene sulfonic acid and their salts, e.g. sodium, potassium, ammonium salts.

Of the sulfonated C12 to C22 carboxylic acids and their aforesaid salts, sulfonated 9-octadecanoic acid, disodium 2-sulfo $C_{12}$–$C_{18}$ fatty acid salts and sodium methyl-2-sulfo $C_{12}$–$C_{16}$ esters are preferred.

A preferred salt of naphthalene sulfonic acid is sodium alkyl naphthalene sulfonate.

Preferred salts of C8 to C22 alkyl sulfonic acids are sodium octyl (C8) sulfonate, sodium C14–C17 sec-alkyl sulfonate, and the sodium salts of 1-octane sulfonic acid, 1-decane sulfonic acid, and tridecane sulfonic acid.

Of the aforesaid C8 to C18 alkyl sulfates, sodium lauryl sulfate and sodium octyl sulfate are preferred.

Of the alkyl or alkenyl esters or diesters of sulfosuccinic acid in which the alkyl or alkenyl groups independently contain from six to eighteen carbon atoms and alkali metal, ammonium, calcium and magnesium salts thereof, disodium laureth sulfosuccinate and sodium dioctyl sulfosuccinate are preferred.

The C6 to C22 alkyl diphenyl oxide sulfonic acids and alkali metal, ammonium, calcium and magnesium salts thereof are required if the solution is to be an effective virucide. In such formulations, C6 and C10 alkylated sulfonated diphenyl oxide disodium salt are the most preferred. However, also preferred are other alkylated sulfonated diphenyl oxide disodium salts, including dodecyl diphenyl oxide disulfonic acid and disodium 4-dodecylated diphenyloxide sulfonate.

The solution may contain each anionic surfactant alone or in combination with each other. A preferred mixture of anionic surfactants is a combination of dodecyl benzene sulfonic acid and C6 alkylated sulfonated diphenyl oxide disodium salt. A solution according to the invention having these anionic surfactants will serve both as a bactericide and as a virucide.

The anionic surfactant is present in a concentration of from about 0.02 and 5 wt./wt. % and preferably from about 0.08 to about 3.6 wt./wt. %. Again, the higher amounts apply to the concentrate forms of the solution while the lower amounts apply to the ready-to-use forms.

Concentrated forms of the present solution may contain up to about 20 wt./wt. % hydrogen peroxide and preferably up to about 8 wt./wt. %. Ready-to-use preparations may contain from about 0.01 to about 1.0 wt./wt. %. As will be illustrated by the examples which follow, solutions of about 0.5 wt./wt. % are effective in substantially reducing bacterial and/or viral activity.

Solutions having about from about 0.01 to about 1.0 wt./wt %, especially about 0.5 wt./wt. % hydrogen peroxide are suitable for use as household and commercial disinfectants, bactericides and/or virucides, sanitizers and cleaners. Solutions having about 3 to about 4 wt./wt. % are suitable for use as multi-purpose cleaners and bleach alternatives in healthcare facilities, households and commercial facilities. Solutions having about 6 to about 8 wt./wt. % hydrogen peroxide are suitable for use as a sporicides, fungicides, virucides and/or bactericides, broad spectrum sanitizers, general purpose cleaners, and bleach alternatives, particularly in institutional, healthcare and food applications.

Other surfactants, in the form of detergents, emulsifiers or hydrotropes, may be present in the solutions. For example, certain emulsifiers, detergents, and hydrotropes are beneficial for cleaning surfaces with organic matter or grease and for providing stability to the solution. Typically, the emulsifiers, detergents and hydrotropes are present in a total concentration of about 10 to about 30 parts per hundred parts of hydrogen peroxide or up to about 3 wt./wt. % of the solution. Preferably, they are present in a concentration of from about 0.04 to about 2.0 wt./wt. %, and more preferably from about 0.1 to about 2.0 wt./wt. % of the solution.

Preferred emulsifiers and detergents are non-ionic alkylated alkoxylate surfactants, preferably polyoxyethylene surfactants. Preferred polyoxyethylene surfactants are alkyl polyoxyethylene surfactants and alkyl aryl polyoxyethylene surfactants. A preferred alkyl polyoxyethylene surfactant which is a detergent is C6–C10 alkyl, 3.5 moles of ethylene oxide (EO) alcohol ethoxylate (AE) sold in association with the trade-mark Alfonic L610-3.5. Also, preferred alkyl aryl polyoxyethylene surfactants which are emulsifiers are C8 to C16 alkylphenol alkoxylates. These include octyl phenol ethoxylate which is sold in association with the trade mark TRITON X405.

Preferred hydrotropes are alkylated sulfonated diphenyl oxides and alkylated sulfonated diphenyl oxide salts, e.g. C6 alkylated sulfonated diphenyl oxide disodium salt (which is also useful as an anionic surfactant, as noted above).

The pH of the solutions is from about 0.5 to about 6, and more preferably from about 0.7 to about 3.5. Preferred ready-to-use solutions have a pH from about 1.5 to about 3.5. Preferred concentrate versions of the inventive solution have pH values ranging from about 0.7 to about 2. To achieve the preferred pH values, buffering agents may be added to the solution. These buffering agents include phosphoric acid, and sodium or potassium hydroxide, the latter being otherwise known as caustic potash.

Additional additives may be added to further enhance performance. These include a short-chain alcohol, e.g. a C1–C6 alcohol, especially methanol, ethanol, iso-propanol, n-butanol and n-pentanol. Preferably, the short chain alcohol is present in a concentration of from about 0.1 to about 10 wt./wt. % of the solution. Addition of the alcohol is believed to provide improved germicidal activity and additional cleaning ability for organic contaminants.

A corrosion inhibitor may be added for the purpose of improving compatibility of the solution with non-ferrous metals. Examples include a benzotriazole, a hydrobenzotriazole, a carboxybenzotriazole, sodium nitrite, sodium molybdate, sodium gluconate and sodium benzoate and combinations thereof. When included, the preferred concentration is from about 0.05 to about 10 wt./wt. %, more preferably from about 0.05 to about 1.5 wt./wt. %.

Naturally occurring carboxylic acids such as monocarboxylic acids, polycarboxylic acids, and mixtures thereof may be added. These ingredients have known pH buffering, stabilizing and cleaning properties. Preferred monocarboxylic acids are glycolic acid and acetic acid. A preferred polycarboxylic acid is citric acid. When included in the solution, they are present in a concentration of from about 0.05 to about 4.0 wt./wt. % of the solution.

To enhance the marketable qualities of the product, additives such as colouring agents or dyes and scents or fragrances may be added.

Because hydrogen peroxide has a broad spectrum of activity, it is useful in many different applications. In the healthcare field, the solution may be used in hospitals, clinics, laboratories, dental offices, home care and chronic care facilities. It may also be used in food and beverage processing and preparation, animal husbandry, the hospitality industry and for general sanitation, e.g. janitorial services.

A preferred method for preparing the solutions of the present invention comprises adding the phosphorus-based acid(s) and the anionic surfactant(s) and optionally the emulsifiers, detergents and/or hydrotropes to distilled or otherwise purified water prior to the addition of hydrogen peroxide. If there are any other ingredients, e.g. alcohols, scents, colouring agents, dyes, corrosion inhibitors, naturally occurring carboxylic acids, these are preferably added before the hydrogen peroxide. To achieve the desired pH, buffering agents may be added following the addition of the hydrogen peroxide.

It will be clear to the person skilled in the art how to manufacture a powdered concentrate which can be dissolved in water by the end user to produce an aqueous solution according to the invention. Similarly, it will also be clear to the skilled person how to make an even more concentrated disinfecting solution than the solution described herein. Therefore, the present invention is directed also to concentrated versions of the present inventive solution and a powdered concentrate which may be dissolved in water to form the present liquid solution. In powdered form, the hydrogen peroxide is present as sodium percarbonate or sodium perborate. The phosphorus based acid and anionic surfactants are either in salt form or in acid form, as will be understood by the person skilled in the art.

The invention may also be better understood by reference to the following examples:

EXAMPLE I

A solution of the present invention (Solution A) was prepared with 695 parts by weight distilled water, 20 parts by weight 75% phosphoric acid ($H_3PO_4$), 75 parts by weight 50% Briquest 301-50A (trade mark) amino tri(methylene phosphonic acid), 25 parts by weight 45% hydrotrope Dowfax (trade mark) C6 alkylated sulfonated diphenyl oxide disodium salt, 25 parts by weight 98% Biosoft S-100 (trade mark) dodecyl benzene sulfonic acid, 10 parts by weight Triton X-405 70% (trade mark) octyl phenol ethoxylate emulsifier and 150 parts by weight 50% hydrogen peroxide.

The ingredients were mixed in a passivated vessel, with hydrogen peroxide being the last ingredient added to the solution. The pH of the solution was 1.27.

Aliquots of this solution were tested for mycobacterial, sporicidal, fungicidal, bactericidal and virucidal activity and compared against commercially available disinfectants. For testing for bactericidal and virucidal activity, aliquots were diluted with water, with 1 part solution to 15 parts water.

Quantitative carrier tests were conducted on the samples using a first method for testing mycobacterial, sporicidal, fungicidal, and bactericidal activity. A second quantitative carrier test method was employed to test virucidal activity. The first method is the American Society of Testing and Materials ("ASTM") standard quantitative carrier test (ASTM Method E2111-00), described in the publication entitled "Standard Quantitative Test Method to Evaluate the Bactericidal, Fungicidal, Mycobactelicidal and Sporicidal Potencies of Liquid Chemical Germicides", American Society for Testing of Materials, West Conshohocken, Pa. The second Both test methods incorporated the essential requirements of the Canadian General Standards Boards' standard entitled "Assessment of Efficacy of Antimicrobial Agents for Use on Environmental Surfaces and Medical Devices" (CGSB 1997). These methods will now be described.

The inside bottom surface of glass vials was used as the carrier surface for mycobacterial, sporicidal, fungicidal, bactericidal tests. Stainless steel disks were used as the carrier surface for virucidal tests. Silk suture loops were not used because of the extreme difficulty in using them for standardized tests.

All test organisms were first suspended in bovine serum at a final concentration of 5 wt./wt. % of the solution. When the product was to be tested after dilution, water with a standard hardness of 200 ppm as calcium carbonate was used as the diluent. The water was prepared according to the formula in AOAC International (1990).

Phosphate buffer, at pH 7.2, was used to make dilutions of spores and vegetative bacterial cells and to rinse membrane filters in tests for sporicidal and bactericidal tests. The diluent and filter rinse used for mycobacterial and fungicidal tests was sterile normal saline (0.85% sodium chloride). Earle's balance salt solution was used to prepare dilutions of the virus prior to infectivity assays.

The general steps for quantitative analysis of mycobacterial, sporicidal, fungicidal and bactericidal activities of the test disinfectant involved i) inoculating carriers with inserts centred in vials, ii) dyeing the inoculated carriers, iii) removing the inserts, iv) adding a test disinfectant to the inoculated carrier, v) diluting the test disinfectant at the completion of a known exposure time at a known temperature, vi) filtering and vii) placing the filters onto a medium, followed by incubating. The colony forming units (CFU) were then determined.

Control carriers were used in the same manner as test carriers, except that phosphate buffer was applied to the dried inoculum instead of disinfectant in the case of sporicidal and bacterial tests, and sterile saline was applied in the case of mycobactericidal and fungicidal tests. In the tests, there were three control carriers to every seven test carriers.

For virucidal activity, each stainless steel disk received test virus in bovine serum. After the inoculum had dried, it was exposed either to Earle's buffer solution or the test disinfectant for the required contact time and temperature. Each disk was placed in a vial with eluent/diluent and vortexed to recover the inoculum. The control and test eluates were inoculated into cell cultures for virus plaque assays. The plaque forming units (PFU) were then determined. To avoid false positive results, further controls were carried out by exposing the cell monolayers to a non-virucidal and non-cytotoxic dilution of the test products and then using the same monolayers for plaque assays. If the number of plaques on such pre-exposed monolayers was the same as those exposed to Earle's solution, the product was regarded as free from interference. In the tests, there were three control carriers to every five test carriers.

The test results are shown in Tables Ia and Ib.

TABLE Ia bacteria

| Organism | Contact time | CFU** Control | Solution A |
|---|---|---|---|
| ATCC 19659* | 6 hours | $1.96 \times 10^8$ | 0 |
| ATCC 7955* | 6 hours | $3.12 \times 10^7$ | 0 |
| ATCC 15442* | 10 minutes | $1.79 \times 10^6$ | 0 |
| ATCC 15442* | 3 minutes | $1.25 \times 10^6$ | 0 |
| ATCC 15442* | 1 minute | $1.45 \times 10^6$ | 0 |
| ATCC 6538* | 1 minute | $1.40 \times 10^6$ | 0 |
| ATCC 10708* | 1 minute | $1.16 \times 10^6$ | 0 |
| ATCC 15755* | 20 minutes | $1.8610^6$ | 0 |
| ATCC 9533* | 5 minutes | $4.0 \times 10^5$ | 0 |

TABLE Ib viruses

| Organism | Contact time | PFU** Control | Solution A |
|---|---|---|---|
| ATCC VR-192* | 5 minutes | $8.7 \times 10^4$ | 1 |
| ATCC VR-192* | 5 minutes | $8.7 \times 10^4$ | 10 |

*ATCC 19659 *Bacillus subtilis*;
*ATCC 7955 *Clostridium sporogenes*;
*ATCC 15442 *Pseudomonas aeruginosa*;
*ATCC 6538 *Staphylococcus aureus*;
*ATCC 10708 *Salmonella chloreræsuis*;
*ATCC 15755 *Mycobacterium terrae*;
*ATCC 9533 *Trichophyton mentagrophytes*;
*ATCC VR-192* Sabin vaccine strain of polio virus Type I
**CFU = colony forming units; PFU = plaque forming units

EXAMPLE II

Solution A of Example I was tested further, according to a third method which is the AOAC 960.09 method, titled "Germicidal and Detergent Sanitizing Action of Disinfectants", Final Action AOAC XV, 1995, Part 6.3.03 (hereinafter referred to as the "AOAC 960.09 method"). The AOAC 960.09 method is a suspension test standardized by the AOAC, Association of Official Analytical Chemists, which uses a contact time of 30 seconds.

Samples of the organism being tested were mixed with 5% bovine serum. 56 mL portions of Solution A were diluted with 4 liters of 200 ppm synthetic hard water. Each dilute solution was applied to an organism at 20° C. and the organism count per milliliter was determined before application of the solution, and 30 seconds and 60 seconds after application of the solution. The results are shown in Table II.

TABLE II

| Organism | Initial Count | Count 30 sec | Count 60 sec |
| --- | --- | --- | --- |
| ATCC 15442 | $94.5 \times 10^6$ | <10 | <10 |
| ATCC 6538 | $44.5 \times 10^6$ | 218 | 75 |
| ATCC 33592* | $32.3 \times 10^6$ | <10 | <10 |
| ATCC 51575* | $94.5 \times 10^6$ | <10 | <10 |

*ATCC 33592 *Staphylococcus aureus* (methicillin resistant); ATCC 51575 *Enterococcus fæcalis* (vancomycin resistant)

EXAMPLE III

Solution A of Example I was tested further, again in accordance with the AOAC 960.09 method.

Samples of the organism being tested were mixed with 5% bovine serum. The undiluted Solution A was applied to the organisms at 20° C. and the organism count per milliliter was determined before application of the solution, and 30 seconds and 60 seconds after application of the solution. The results are shown in Table III.

TABLE III

| Organism | Initial Count | Count 30 sec | Count 60 sec |
| --- | --- | --- | --- |
| ATCC 10708 | $117 \times 10^6$ | <10 | <10 |
| ATCC 15442 | $94.5 \times 10^6$ | <10 | <10 |
| ATCC 6538 | $44.5 \times 10^6$ | <10 | <10 |
| ATCC 33592 | $79.5 \times 10^6$ | <10 | <10 |
| ATCC 51575 | $32.3 \times 10^6$ | <10 | <10 |

EXAMPLE IV

The test according to Example II (i.e. using the AOAC 960.09 method) was modified, using 50% bovine serum which was added to the organism. 56 mL portions of Solution A were diluted with 4 liters of 200 ppm synthetic hard water. Each dilute solution was applied to an organism at 20° C. and the organism count per milliliter was determined before application of the solution, and 30 seconds and 60 seconds after application of the solution. The results are shown in Table IV.

TABLE IV

| Organism | Initial Count | Count 30 sec | Count 60 sec |
| --- | --- | --- | --- |
| ATCC 15442 | $235 \times 10^6$ | <10 | <10 |
| ATCC 6358 | $115 \times 10^6$ | <10 | <10 |
| ATCC 10708 | $81.3 \times 10^6$ | <10 | <10 |

EXAMPLE V

Tests were carried out to determine the cleaning efficiency of diluted solutions of Solution A compared to commercially available cleaners. A fourth test, namely Procedure CAN/CGSB 2.1, Method 20.3 was used, in which synthetic soil, of brown iron oxide pigment, kerosene, Stoddard solvent, white petroleum jelly, lubricating oil and shortening, was applied to white vinyl tiles. As a control, a 1% CGSB standard detergent in 125 ppm hard water, was used.

One portion of Solution A was diluted in 125 ppm hard water to form Solution B, which contained about 0.06% hydrogen peroxide. Another portion of Solution A was diluted in 125 ppm hard water to form Solution C, which contained about 0.01% hydrogen peroxide. A sample of commercial sodium hypochlorite bleach was diluted 1:20 to form Solution D.

The contaminated tiles were cleaned with 50 mL of each solution being tested and cleaning efficiency values were based on reflectance measurements. The results are shown in Table V.

TABLE V

| Solution | Efficiency (%) |
| --- | --- |
| Solution B (0.06% $H_2O_2$) | 94.6 |
| Solution C (0.01% $H_2O_2$) | 93.7 |
| Solution D (Na hypochlorite) | 11.3 |
| Standard Detergent | 77.2 |
| Distilled water | 11.4 |

EXAMPLE VI to X

Experiments were conducted to study the contribution of individual components of the present inventive formulation towards overall efficacy. The following legend applies to assist in the understanding of Examples VI to X below.

Phosphorous-based Compounds $H_3PO_4$=phosphoric acid

STPP=sodium tripolyphosphate

BRIQUEST ADPA-60AW (HEDP)=1-hydroxyethylidene-1,1,-diphosphonic acid

Briquest 301-50A (ATMP)=amino tri(methylene phosphonic acid)

Anionic Surfactants

Biosoft S-100 (DDBSA)=dodecyl benzene sulfonic acid

Dowfax C10L C10=C10 alkylated sulfonated diphenyl oxide disodium salt

Petro ULF (ANS)=sodium alkyl naphthalene sulfonate

Bioterge PAS-8 (SOS)=sodium octyl sulfonate

Hostapur SAS-30=sodium C14–C17 sec-alkyl sulfonate

Stepanol WAC (SLS)=sodium lauryl sulfate

Standapol LF (SOS)=sodium octyl sulfate

Stepan Mild SL3 (SLSS)=disodium laureth sulfosuccinate

DOWFAX hydrotrope=C6 alkylated sulfonated diphenyl oxide disodium salt

Alpha-Step MC-48 (SMSE/SFA) =solution containing SMSE and SFA (relative ratio of components not given by manufacturer)

SMSE=sodium methyl 2-sulfo $C_{12}$–$C_{16}$ ester

SFA=disodium 2-sulfo $C_{12}$–$C_{18}$ fatty acid salt

Non-ionic Surfactants (Emulsifiers)

Alfonic L610-3.5=C6–C10 alkyl, 3.5 moles of ethylene oxide (EO) alcohol ethoxylate (AE)

TRITON X-405 (OPE)=octyl phenol ethoxylate

Anionic Surfactants (Hydrotropes)

C6 DOWFAX hydrotrope=C6 alkylated sulfonated diphenyl oxide disodium salt

EXAMPLE VI

Formulations A1 to A5 were prepared and tested on the gram positive surrogate *Staphylococcus aureus* (also referred to as ATCC 6538) according to the ASTM Method E2111-00 and the AOAC 960.09 method discussed above under Examples I and II, respectively. The results were compiled and are shown in Table VI below.

TABLE VI

| INGREDIENT - [%] w/w | A1 % w/w | A2 % w/w | A3 % w/w | A4 % w/w | A5 % w/w |
|---|---|---|---|---|---|
| $H_3PO_4$ (75%) | 0.15 | 0.15 | 0.15 | 0.27 | 0.15 |
| | 0.11 | 0.11 | 0.11 | 0.20 | 0.11 |
| BRIQUEST ADPA-60AW (60% HEDP) | 0.47 | 0.47 | 0.47 | — | 0.48 |
| | 0.28 | 0.28 | 0.28 | — | 0.29 |
| C6 DOWFAX Hydrotrope (45%) | 0.18 | 0.18 | 0.18 | — | 0.18 |
| | 0.08 | 0.08 | 0.08 | — | 0.08 |
| BIOSOFT S-100 (98% DDBSA) | 0.18 | 0.18 | — | 0.18 | 0.18 |
| | 0.18 | 0.18 | — | 0.18 | 0.18 |
| TRITON X-405 (70% OPE) | 0.08 | 0.08 | 0.08 | — | 0.05 |
| | 0.06 | 0.06 | 0.06 | — | 0.04 |
| $H_2O_2$ (50%) | 2.00 | — | 2.00 | 2.00 | 1.10 |
| | 1.00 | — | 1.00 | 1.00 | 0.55 |
| pH | 1.91 | 1.93 | 1.94 | 1.97 | 1.91 |
| Water | to 100 | to 100 | to 100 | to 100 | to 100 |
| Germicidal Results | | | | | |
| AOAC 960.09 suspension test, contact time 30 seconds | 6.22 | 6.04 | NM | 6.22 | >6 |
| ASTM Method E2111-00 carrier test, Contact time: 3 min | 6.22 | 3.43 | 1.66 | 6.22 | >6 |

Table VI. Single-factor experiments with 1% and 0.55% hydrogen peroxide. Numbers shown under germicidal results are $Log_{10}$ reduction in the number of viable organisms. NM: not measurable due to substantial growth - plates had colonies too numerous to count (typically a reduction of less than $3Log_{10}$). A 6-$Log_{10}$ reduction is considered effective as a disinfectant.

The AOAC 960.09 method gives rise to more favourable disinfection results than the ASTM Method E2111-00 and involves adding a small drop of the organism inoculum to a tube of germicide solution and mixing for the specified contact time. The microbes are suspended in and surrounded entirely by the germicide solution. The ASTM Method E2111-00 evaluates bactericidal activity of liquid chemical germicides to be used on non-porous environmental surfaces and is more challenging, giving rise to less favorable disinfection results than the AOAC 960.09 test. This method is used in higher risk applications where the presence of even low levels of bacteria cannot be tolerated, such as in the disinfection of surgical instruments used in the health care industry. The ASTM Method E2111-00 involves drying the microbe inoculum on the surface of a carrier (a small glass or steel disc or plate) and then immersing the carrier in the germicide solution. The germicide solution must penetrate a large lumped mass of organism/culture broth in order to effectively reach all microbes and effect a good kill.

Although Formulation A4 contains 0.27 wt./wt. % phosphoric acid as compared to 0.15 wt./wt. % of Formulations A1 to A3, and A5, it has been found in separate experiments (not presently shown) that, at these concentration levels, phosphoric acid does not contribute to the bactericidal activity of the solution. In the above experiments, the phosphoric acid is used to buffer the solution to pH levels slightly below 2 as shown.

Formulations A1, A4 and A5 are exemplary embodiments of the present invention containing 1.00, 1.00 and 0.55 wt./wt. % hydrogen peroxide, respectively. These solutions result in a greater than 6 $Log_{10}$ reduction in bacteria counts, showing them to be effective disinfectants using both methods of testing.

Formulation A2 is similar to formulation A1 except that the hydrogen peroxide has been omitted. Using the AOAC 960.09 suspension test, it can be seen that the formulation exhibits a high level of germicidal activity which is attributable to the anionic surfactant, dodecyl benzene sulfonic acid (DDBSA). This is quite expected as concentrations of DDBSA as low as 200 ppm are known to be effective in sanitizing (cf. Lopes, J. A. (1986) "Evaluation of dairy and food plant sanitizers against *Salmonella typhimurium* and *Listeria monocytogenes*", J. Dairy Sci., 69, 2791–2796). However, when the more challenging ASTM quantitative carrier test is used, it is apparent that both the DDBSA and the hydrogen peroxide are necessary to achieve disinfection.

The results for formulation A3 show that the anionic surfactant, DDBSA, is necessary for disinfection.

EXAMPLE VII

Formulations B1 to B3 were prepared and tested on the gram positive surrogate *Staphylococcus aureus* (ATCC 6538) according to the ASTM Method E-2111-00. The results were compiled and are shown in Table VII below.

TABLE VII

| INGREDIENT [% w/w] | B1 % w/w | B2 % w/w | B3 % w/w |
|---|---|---|---|
| Briquest ADPA-60AW (60% HEDP) | 0.48 | — | — |
| | 0.29 | — | — |
| Briquest 301-50A (50% ATMP) | — | 0.58 | — |
| | — | 0.29 | — |
| STPP (90% sodium tripolyphosphate) | — | — | 0.32 |
| | — | — | 0.29 |
| C6 Dowfax Hydrotrope (45%) | 0.18 | 0.18 | 0.18 |
| | 0.08 | 0.08 | 0.08 |
| Alfonic L610-3.5 (100% AE) | 0.05 | 0.05 | 0.05 |
| | 0.05 | 0.05 | 0.05 |
| Hydrogen Peroxide (50%) | 1.10 | 1.10 | 1.10 |
| | 0.55 | 0.55 | 0.55 |
| Biosoft S-100 (98% DDBSA) | 0.18 | 0.18 | 0.18 |
| | 0.18 | 0.18 | 0.18 |
| pH | about 2 | about 2 | about 2 |
| Water | to 100 | to 100 | to 100 |
| Germicidal results | | | |
| ASTM Method E-2111-00 carrier test, Contact time: 3 min | 6.85 | 6.85 | 6.56 |

Table VII. Efficacy of formulations based on different phosphorous containing acids. Actual concentrations calculated and shown in bold-faced font. Numbers shown under germicidal results are $Log_{10}$ reduction in the number of viable organisms. A minimum of 6- $Log_{10}$ reduction is considered effective as a disinfectant.

Formulations B1 to B3 are exemplary embodiments of the present invention containing 0.55 wt./wt. % hydrogen peroxide. These solutions result in a greater than 6 $Log_{10}$ reduction in bacteria counts, showing them to be effective disinfectants.

Formulations B1, B2 and B3 differ only in the type of phosphorous based acid that is utilized. In formulation B1, the phosphorous-based acid employed is 1-hydroxyethylidene-1,1,-diphosphonic acid (HEDP, a diphosphonic acid). Formulation B2 has been prepared with amino tri(methylene phosphonic acid) (ATMP, a triphosphonic acid), while formulation B3 is not based on a phosphonic acid, but rather on another phosphorous-based acid, tripolyphosphoric acid (a polymerized form of phosphoric acid). Phosphoric acid and tripolyphosphoric acid are derivatives of phosphorous oxides in which the phosphorous atom is in the +5 oxidation state. It is believed that all such derivatives will be useful in the present inventive formulation. These experiments demonstrate that other phosphorous-based acids, alone, can be employed in preparation of the claimed composition without a significant drop in biocidal efficacy.

EXAMPLE VIII

Formulations C1 to C9, based on 0.55 wt./wt. % hydrogen peroxide, were prepared and tested in accordance with ASTM Method E-2111-00 against *Staphylococcus aureus* (ATCC 6538). The only difference among formulations C1 to C9 is in the identity of anionic surfactant used. Formulation C10 was prepared and tested as a control. The results are shown in Table VIII below.

TABLE VIII

| INGREDIENT (% w/w) | FORMULATION | | | | |
|---|---|---|---|---|---|
| | C1 % w/w | C2 % w/w | C3 % w/w | C4 % w/w | C5 % w/w |
| Phosphoric acid (75%) | 0.15 0.11 | 0.15 0.11 | 0.15 0.11 | 0.15 0.11 | 0.15 0.11 |
| Briquest ADPA-60AW (60%) | 0.48 0.29 | 0.48 0.29 | 0.48 0.29 | 0.48 0.29 | 0.48 0.29 |
| C6 Dowfax Hydrotrope (45%) | 0.18 0.08 | 0.18 0.08 | 0.18 0.08 | 0.18 0.08 | 0.18 0.08 |
| Alfonic L610-3.5 (100%) | 0.05 0.05 | 0.05 0.05 | 0.05 0.05 | 0.05 0.05 | 0.05 0.05 |
| Hydrogen Peroxide (50%) | 1.10 0.55 | 1.10 0.55 | 1.10 0.55 | 1.10 0.55 | 1.10 0.55 |
| Dowfax C10L C10 (45%) | — | 0.39 0.18 | — | — | — |
| Stepan Mild SL3 (SLSS) (32%) | — | — | 0.54 0.17 | — | — |
| Petro ULF (ANS) (95%) | — | — | — | 0.18 0.17 | — |
| Stepanol WAC (SLS) (29%) | — | — | — | — | 0.55 0.16 |
| Biosoft S-100 (98%) | 0.18 0.18 | — | — | — | — |
| pH | about 2 | about 2 | about 2 | about 2 | about 2 |
| Water | to 100 | to 100 | to 100 | to 100 | to 100 |
| Germicidal activity | | | | | |
| ASTM Method E-2111-00, Contact time: 3 min; *Staph. aureus* | 6.76 | 6.76 | 5.91 | 6.76 | 6.83 |

| INGREDIENT (% w/w) | FORMULATION | | | | |
|---|---|---|---|---|---|
| | C6 % w/w | C7 % w/w | C8 % w/w | C9 % w/w | C10 % w/w |
| Phosphoric acid (75%) | 0.15 0.11 | 0.15 0.11 | 0.15 0.11 | 0.15 0.11 | 0.15 0.11 |
| Briquest ADPA-60AW (60% HEDP) | 0.48 0.29 | 0.48 0.29 | 0.48 0.29 | 0.48 0.29 | 0.48 0.29 |
| C6 Dowfax Hydrotrope (45%) | 0.18 0.08 | 0.18 0.08 | 0.18 0.08 | 0.18 0.08 | 0.18 0.08 |
| Alfonic L610-3.5 (100% AE) | 0.05 0.05 | 0.05 0.05 | 0.05 0.05 | 0.05 0.05 | 0.05 0.05 |
| Hydrogen Peroxide (50%) | 1.10 0.55 | 1.10 0.55 | 1.1 0.55 | 1.1 0.55 | 1.1 0.55 |
| Hostapur SAS-30 (30% SAS) | — | — | 0.60 0.18 | — | — |
| Standapol LF (35% SOS) | — | — | — | 0.51 0.18 | — |
| Alpha-Step MC-48 (37% SMSE/SFA) | — | 0.42 0.16 | — | — | — |
| Bioterge PAS 8 (SOS) (38%) | 0.45 0.17 | — | — | — | — |
| pH | about 2 | about 2 | about 2 | about 2 | about 2 |
| Water | to 100 | to 100 | to 100 | to 100 | to 100 |
| Germicidal activity | | | | | |
| ASTM Method E-2111-00 Contact time: 3 min; *Staph. aureus* | 6.76 | 6.21 | 5.45 | 6.4 | NM |

Table VIII. Efficacy of formulations based on different anionic surfactants. Actual concentrations calculated and shown in bold-faced font. Numbers shown under germicidal results are $Log_{10}$ reduction in the number of viable organisms. A minimum of 6-$Log_{10}$ reduction is considered effective as a disinfectant. NM means not measurable due to substantial growth - plates had colonies too numerous to count (typically a reduction of less than 3logs).

All formulations C1 to C10 contain C6 alkylated sulfonated diphenyl oxide disodium salt which is both a hydrotrope and an anionic surfactant belonging to the class of anionic surfactants defined herein as C6 to C22 alkyl diphenyl oxide sulfonic acids and alkali metal, ammonium, calcium and magnesium salts thereof. This member of the class contributes to virucidal rather than bactericidal properties of the present inventive formulation, as will be discussed further below in Example X. For the purposes of this Example IX, C10 acts as a control.

Formulation C1 contains dodecyl benzene sulfonic acid which belongs to the group consisting of C8 to C16 alkyl aryl sulfonic acids and alkali metal, ammonium, calcium and magnesium salts thereof.

Formulation C2 contains C10 alkylated sulfonated diphenyl oxide disodium salt which belongs to the group defined as C6 to C22 alkyl diphenyl oxide sulfonic acids and alkali metal, ammonium, calcium and magnesium salts thereof.

Formulation C3 contains disodium laureth sulfosuccinate which is a member of the group defined as alkyl or alkenyl esters or diesters of sulfosuccinic acid in which the alkyl or alkenyl groups independently contain from six to eighteen carbon atoms and alkali metal, ammonium, calcium and magnesium salts thereof. More specifically, formulation C3 is based on an ethoxylated ester of sulfosuccinic acid, with a hydrophobic chain of equivalent length $C_8$.

Formulation C4 contains sodium alkyl naphthalene sulfonate which belongs to the group defined as naphthalene sulfonic acids and alkali metal, ammonium, calcium and magnesium salts thereof.

Formulations C5 and C9 contain sodium lauryl sulfate and sodium octyl sulfate, respectively, which belong to the class identified herein as alkali metal, ammonium, calcium and magnesium C8 to C18 alkyl sulfates. More specifically, formulation C5 is based on a sulfated $C_{12}$ alcohol.

Formulations C6 and C8 contain sodium octyl sulfonate and sodium C14–C7 sec-alkyl sulfonate, respectively, which belong to the group consisting of C8 to C22 alkyl sulfonic acids and alkali metal, ammonium, calcium and magnesium salts thereof.

Formulation C7 contains a mixture of sodium methyl 2-sulfo $C_{12}$–$C_{16}$ ester and disodium 2-sulfo $C_{12}$–$C_{18}$ fatty acid salt which are members of the class consisting of sulfonated C12 to C22 carboxylic acids and alkali metal, ammonium, calcium and magnesium salts thereof. More specifically, formulation C7 is an example of a sulfonated carboxylic acid and a sulfonated methyl-ester of that acid.

Formulations C1, C2, C4 and C6 comprise surfactants which have a sulfonic acid moiety as the polar head, and hydrophobic chains of lengths equivalent to $C_{15}$–$C_{16}$, $C_{10}$–$C_{12}$, $C_{8}$–$_{12}$, and $C_8$, respectively.

Formulations C1, C2, C4, C5, C6, C7, and C9 are all effective as disinfectants as they were able to achieve a greater than 6 $\log_{10}$ reduction in bacterial counts. Although formulations C3 and C8 are not so effective as to be considered disinfectants, they are nonetheless highly effective, achieving a greater than 5 $\log_{10}$ reduction in bacterial counts. In contrast, formulation C10 resulted in bacterial counts which were too numerous to count, i.e. less than a 3 $\log_{10}$ reduction in bacterial counts. The above tests show that formulations according to the present invention exhibit bactericidal activity.

EXAMPLE IX

Formulations D1 to D3 according to the present invention were prepared and tested using ASTM Method E-2111-00 on the gram positive surrogate *Staphylococcus aureus* (ATCC 6538). The only difference among these formulations is the pH value and amount of NaOH buffer added to achieve the pH value. The results were compiled and are shown in Table IX below.

TABLE IX

| INGREDIENT (% w/w) | D1 % w/w | D2 % w/w | D3 % w/w |
|---|---|---|---|
| Phosphoric acid (75%) | 0.15 | 0.15 | 0.15 |
| | 0.11 | 0.11 | 0.11 |
| Briquest ADPA-60AW (60%) | 0.48 | 0.48 | 0.48 |
| | 0.29 | 0.29 | 0.29 |
| C6 Dowfax Hydrotrope (45%) | 0.18 | 0.18 | 0.18 |
| | 0.08 | 0.08 | 0.08 |
| Alfonic L610-3.5 (100%) | 0.05 | 0.05 | 0.05 |
| | 0.05 | 0.05 | 0.05 |
| Hydrogen Peroxide (50%) | 1.10 | 1.10 | 1.10 |
| | 0.55 | 0.55 | 0.55 |
| Biosoft S-100 (DDBSA) (98%) | 0.18 | 0.18 | 0.18 |
| | 0.18 | 0.18 | 0.18 |
| NaOH (50%) to pH shown | pH 3.8 | pH 5.0 | PH 6.0 |
| Water | to 100 | to 100 | to 100 |
| Germicidal activity | | | |
| ASTM Method E-2111.00 Contact time: 3 min | 6.57 | 6.14 | 5.03 |

Table IX. Efficacy of formulations at differing pH. Actual concentrations calculated and shown in bold-faced font. Numbers shown under germicidal results are $\text{Log}_{10}$ reduction in the number of viable organisms. A minimum of 6- $\text{Log}_{10}$ reduction is considered effective as a disinfectant.

The results in Table IX show that the composition is effective over a wide pH range up to at least 6.0. However, germicidal activity is seen to exhibit an inverse dependence on pH. For practical purposes the maximum limit for efficacy has been set at a pH of about 6.0.

EXAMPLE X

Formulations E1 to E5 containing 0.55 wt./wt. % hydrogen peroxide, were tested against the non-enveloped polio virus ATCC VR-192 in accordance with the second test described under Example I. The results are included in Table X below.

TABLE X

| INGREDIENT (% w/w) | E1 % w/w | E2 % w/w | E3 % w/w | E4 % w/w | E5 % w/w |
|---|---|---|---|---|---|
| Phosphoric acid (75%) | 0.15 | 0.15 | 0.15 | 0.15 | — |
| | 0.11 | 0.11 | 0.11 | 0.11 | — |
| Briquest ADPA-60AW (60% HEDP) | — | 0.48 | 0.48 | 0.48 | 0.48 |
| | — | 0.29 | 0.29 | 0.29 | 0.29 |
| C6 Dowfax Hydrotrope (45%) | 0.18 | — | 0.18 | 0.18 | 0.18 |
| | 0.08 | — | 0.08 | 0.08 | 0.08 |
| Alfonic L610-3.5 (100% AE) | 0.05 | 0.05 | — | 0.05 | 0.05 |
| | 0.05 | 0.05 | — | 0.05 | 0.05 |
| Hydrogen Peroxide (50%) | 1.1 | 1.1 | 1.1 | 1.1 | 1.1 |
| | 0.55 | 0.55 | 0.55 | 0.55 | 0.55 |
| Biosoft S-100 (98% DDBSA) | 0.18 | 0.18 | 0.18 | — | 0.18 |
| | 0.18 | 0.18 | 0.18 | — | 0.18 |
| Phosphoric acid (75%) (for adjusting pH to about 1.8) | 0.08 | — | — | 0.15 | — |
| | 0.06 | — | — | 0.11 | — |
| Water | to 100 | to 100 | to 100 | to 100 | to 100 |
| Germicidal activity | | | | | |
| Quantitative virus test (CGSB 1997) Contact time: 5 min; Log10 reduction in Polio Virus | 1.72 | 0.08 | 4.12 | 4.55 | 4.24 |

Table X. Efficacy results versus polio virus. Actual concentrations calculated and shown in bold-faced font. A minimum 3-$\text{Log}_{10}$ reduction is considered effective as a virucide.

Only formulations E3 to E5 are effective as virucides since only they were able to achieve a greater than 3 $\log_{10}$ reduction in viral counts. Table X demonstrates that virucidal activity is highly dependant on the 1-hydroxyethylidene-1,1,-diphosphonic acid and the C6 alkylated sulfonated diphenyl oxide disodium salt, as shown by the results for formulations E1 and E2. Furthermore, formulation E4 shows that dodecylbenzene sulfonic acid, an indispensable component for activity versus vegetative bacteria, is not required for virucidal activity. Formulation E3 shows that virucidal activity is not affected by the presence of the non-ionic surfactant, Alfonic L610-3.5 (C6–C10 alkyl, 3.5 moles of ethylene oxide (EO) alcohol ethoxylate (AE). Formulation E5 shows that phosphoric acid is not a requirement for virucidal activity.

What is claimed is:

1. An aqueous solution having a pH of from about 0.5 to about 6 and consisting essentially of i) hydrogen peroxide in a concentration of from about 0.01 to about 20 wt./wt. % of the solution, ii) at least one phosphorus-based acid in a concentration range of from about 0.05 to about 8 wt./wt. % of the solution, and iii) at least one anionic surfactant selected from the group consisting of C8 to C16 alkyl aryl sulfonic acids and alkali metal, ammonium, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 5 wt./wt. % of the solution.

2. An aqueous solution according to claim 1 wherein the phosphorus-based acid is selected from the group consisting of the derivatives of phosphorous oxides in which the phosphorous atom is in the +5 oxidation state, phosphonic acids having 1 to 5 phosphonic acid groups and salts thereof, and mixture thereof.

3. A solution according to claim 2 wherein the phosphorus-based acid is selected from the group consisting of phosphoric acid, sodium tripolyphosphate, 1-hydroxyethylidene-1,1,-diphosphonic acid, amino tri (methylene phosphonic acid), diethylenetriaminepenta- (methylene phosphonic acid), 2-hydroxyethylimino bis (methylene phosphonic acid), ethylene diamine tetra (methylene phosphonic acid), and mixtures thereof.

4. A solution according to claim 3 wherein the phosphorus-based acid is selected from the group consisting of phosphoric acid, 1-hydroxyethylidene-1,1,-diphosphonic acid, and mixtures thereof.

5. A solution according to claim 1 wherein the anionic surfactant is selected from the group consisting of dodecyl benzene sulfonic acid and alkali metal, ammonium, calcium and magnesium salts thereof, C6 to C22 alkyl diphenyl oxide sulfonic acid and alkali metal, ammonium, calcium and magnesium salts thereof, and mixtures thereof.

6. A solution according to claim 5 wherein the anionic surfactant is selected from the group consisting of dodecyl benzene sulfonic acid and an alkali metal salt thereof, a C6 alkylated sulfonated diphenyl oxide disodium salt, and mixtures thereof.

7. A solution according to claim 1 wherein the solution has a hydrogen peroxide concentration of from about 0.5 to about 8 wt./wt. % of the solution.

8. A solution according to claim 1 wherein the phosphorus-based acid is present in a concentration of from about 0.2 to about 8 wt./wt. % of the solution.

9. A solution according to claim 1 wherein the anionic surfactant is present in a concentration of from about 0.08 to about 5 wt./wt. % of the solution.

10. A solution according to claim 1 having a pH of from about 0.7 to about 3.5.

11. A concentrated solution which can be diluted with water to produce a solution according to claim 1.

12. A powdered formulation which can be dissolved in water to produce a solution according to claim 1.

13. A solution according to claim 1 wherein the solution has a hydrogen peroxide concentration of from about 0.05 to about 8 wt./wt. % of the solution.

14. An aqueous solution having a pH of from about 0.5 to about 6 and consisting essentially of i) hydrogen peroxide in a concentration of from about 0.1 to about 20 wt./wt. % of the solution, ii) at least one phosphorus-based acid in a concentration range of from about 0.05 to about 8 wt./wt. % of the solution, iii) at least one anionic surfactant selected from the group consisting of C8 to C16 alkyl aryl sulfonic acids and alkali metal, ammonium, calcium and magnesium salts thereof, sulfonated C12 to C22 carboxylic acids and alkali metal, ammonium calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 5 wt./wt. % of the solution, and iv) an additional component selected from the group consisting of emulsifiers, hydrotropes, detergents and mixtures thereof in a concentration of from about 0.04 to about 3 wt./wt. % of the solution.

15. A solution according to claim 14 wherein the emulsifiers and detergents are polyoxyethylene surfactants.

16. A solution according to claim 14 wherein the hydrotrope is selected from the group consisting of alkylated sulfonated diphenyl oxides, alkylated sulfonated diphenyl oxide salts, and mixtures thereof.

17. A solution according to claim 14 containing a C6 alkylated sulfonated diphenyl oxide disodium salt.

18. An aqueous solution having a pH of from about 0.5 to about 6 and consisting essentially of i) hydrogen peroxide in a concentration of from about 0.01 to about 20 wt./wt. % of the solution, ii) at least one phosphorus-based acid in a concentration range of from about 0.05 to about 8 wt./wt. % of the solution, iii) at least one anionic surfactant selected from the group consisting of C8 to C16 alkyl aryl sulfonic acids and alkali metal, ammonium, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 5 wt./wt. % of the solution, and iv) a corrosion inhibitor in a concentration of from about 0.05 to about 10 wt./wt. % of the solution.

19. An aqueous solution having a pH of from about 0.5 to about 6 and consisting essentially of i) hydrogen peroxide in a concentration of from about 0.01 to about 20 wt./wt. % of the solution, ii) at least one phosphorus-based acid in a concentration range of from about 0.05 to about 8 wt./wt. % of the solution, iii) at least one anionic surfactant selected from the group consisting of C8 to C16 alkyl aryl sulfonic acids and alkali metal, ammonium, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 5 wt./wt. % of the solution, and iv) an monocarboxylic acid, a polucarboxylix acid, or mixtures thereof, in a concentration of from about 0.05 to about 4 wt./wt. % of the solution.

20. An aqueous solution having a pH of from about 0.5 to about 6 and consisting essentially of i) hydrogen peroxide in a concentration of from about 0.01 to about 20 wt./wt. % of the solution, ii) at least one phosphorus-based acid in a concentration range of from about 0.05 to about 8 wt./wt. % of the solution, iii) at least one anionic surfactant selected from the group consisting of C8 to C16 alkyl aryl sulfonic acids and alkali metal, ammonium, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 5 wt./wt. % of the solution, and iv) an alcohol comprising one to six carbon atoms in a concentration of from about 0.1 to about 10 wt./wt. % of the solution.

21. An aqueous solution having a pH of from about 0.7 to about 3.5 and consisting essentially of i) hydrogen peroxide in a concentration of from about 0.01 to about 20 wt./wt. % of the solution, ii) a phosphonic acid having from 1 to 5 phosphonic acid groups in a concentration of from about 0.2 to about 8 wt./wt. % of the solution, iii) an anionic alkyl aryl sulfonic acid in a concentration of from about 0.08 to about 5 wt./wt. % of the solution, and iv) an additional component selected from the group consisting of emulsifiers, hydrotropes, detergents and mixtures thereof in a concentration of from about 0.04 to about 3 wt./wt. % of the solution, said additional component including at least one polyoxyethylene surfactant and a alkylated sulfonated diphenyl oxide salt.

* * * * *

UNITED STATES PATENT AND TRADEMARK OFFICE
CERTIFICATE OF CORRECTION

PATENT NO. : 6,803,057 B2
DATED : October 12, 2004
INVENTOR(S) : Ramirez et al.

It is certified that error appears in the above-identified patent and that said Letters Patent is hereby corrected as shown below:

Column 18,
Line 56, "polucarboxylix" should read -- polycarboxylic --.

Signed and Sealed this

Twenty-first Day of June, 2005

JON W. DUDAS
*Director of the United States Patent and Trademark Office*